United States Patent [19]
Bock

[11] Patent Number: 5,827,064
[45] Date of Patent: Oct. 27, 1998

[54] ORBITALLY OR RECIPROCALLY VIBRATING METHOD FOR INTERPROXIMAL PLAQUE REMOVAL

[75] Inventor: Robert T. Bock, Brewster, N.Y.

[73] Assignee: Sonex International Corp., Brewster, N.Y.

[21] Appl. No.: 872,291

[22] Filed: Jun. 10, 1997

Related U.S. Application Data

[63] Continuation-in-part of Ser. No. 705,766, Aug. 30, 1996, Pat. No. 5,738,575.

[51] Int. Cl.$^6$ ..................................................... A61C 15/00
[52] U.S. Cl. ......................... 433/216; 433/118; 433/119; 433/222; 15/167.1
[58] Field of Search .................................. 433/216, 118, 433/119, 222, 223; 15/167.1, 22.1

[56] References Cited

U.S. PATENT DOCUMENTS

| | | |
|---|---|---|
| 4,787,847 | 11/1988 | Martin et al. ............................. 433/216 |
| 5,000,684 | 3/1991 | Odrich ..................................... 433/118 |
| 5,071,348 | 12/1991 | Woog ...................................... 433/118 |
| 5,138,733 | 8/1992 | Bock ....................................... 433/216 |
| 5,573,020 | 11/1996 | Robinson ................................. 433/118 |

Primary Examiner—John J. Wilson

[57] ABSTRACT

Improved methods and apparatus for the removal of plaque from interproximal areas of the dental anatomy and from periodontal pockets. An reciprocal or orbital vibratory motion about the longitudinal axis of the bristles is utilized to impart frictional forces from a multitude of bristles positioned within the interproximal area of two adjacent teeth and in the periodontal pockets of the gum. An advanced embodiment utilizes ultrasonically enhanced bristle tufts to transmit ultrasonic vibrations into the gingival fluids in the periodontal pockets, producing standing ultrasonic waves within the gingival fluids which augments and enhances the plaque removal capability of the reciprocally or orbitally vibrating nylon bristles.

3 Claims, 6 Drawing Sheets

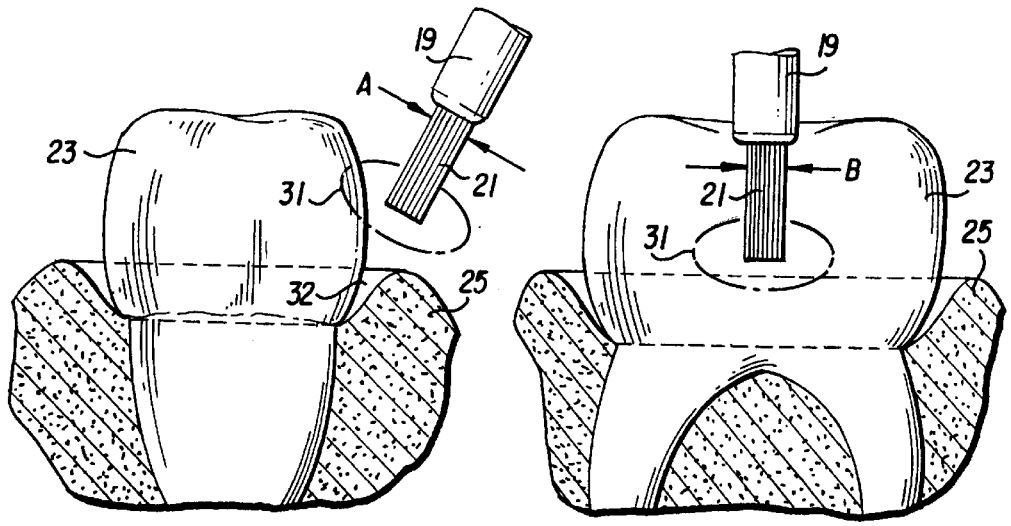
FIG. 4A FIG. 4B
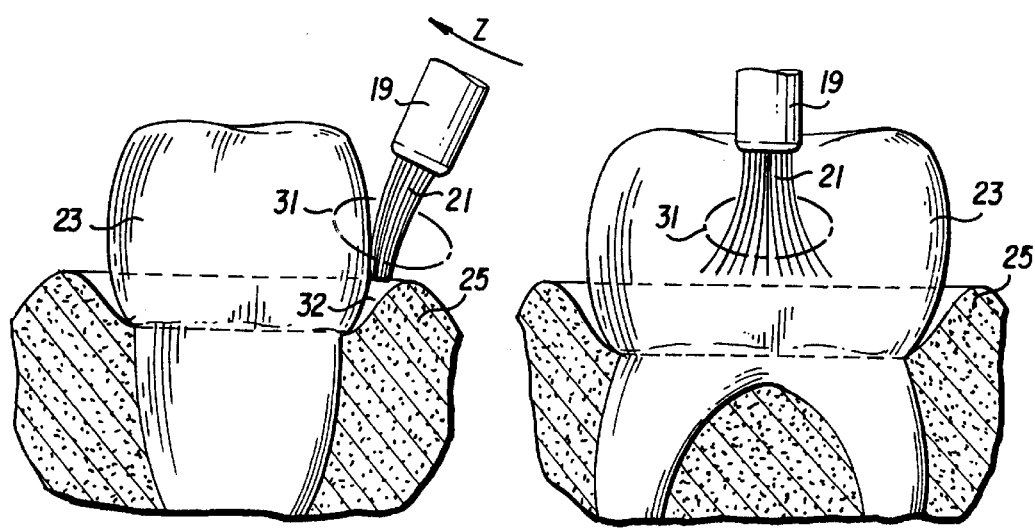
FIG. 4C FIG. 4D

ORBITALLY OR RECIPROCALLY VIBRATING METHOD FOR INTERPROXIMAL PLAQUE REMOVAL

RELATED APPLICATION

This application is a continuation-in-part of U.S. patent application Ser. No. 08/705,766 filed Aug. 30, 1996, now U.S. Pat. No. 5,738,575, entitled Orbitally Vibrating Method and Apparatus for Interproximal Plaque Removal.

BACKGROUND

1. Field of Invention

This invention relates to improved dental hygiene devices for removing plaque from the interproximal areas between teeth, teeth and gums, implants and the prosthesis, teeth and orthodontic appliances, and in particularly from the periodontal pockets of the gums. More particularly the invention is concerned with a method an apparatus utilizing a small tuft of toothbrush filaments vibrated in an orbital or reciprocal motion to facilitate the easy entrance of the filaments within the interproximal areas and to break loose and remove stubborn plaque bacteria from within.

2. Description of prior art.

Numerous attempts has been made in the past to find the ideal method of plaque removal from interproximal areas. First and foremost the experimentation centered upon various toothbrush bristle and tuft configurations to allow better penetration of the bristles into the interproximal areas. As shown in FIG. 6 the corner bristle tufts 26 of the common toothbrush can not penetrate the depth of the periodontal pockets deeper than 1 mm due to their multitufted design, wherein the penetration of a single tuft of bristles 26 into the periodontal pocket 32 is prevented by the contact between the other tufts 26 and the teeth 23 and or the gums 25. Dental floss can be placed between the teeth, but can not be placed or maneuvered into the periodontal pockets 32 on the lingual and facial areas of the teeth.

The next generation of devices developed were the interproximal brushes utilizing a twisted metal spine which supports the radially extending filaments in a typically conical shape. Most of these brushes are held in a pencil like holder by their twisted metal spine and moved into the interproximal areas by the manual manipulation of the user. These interproximal brushes are useful only in largest gaps between the teeth. Due to the design of the twisted wire spine and the radially extending bristles, interproximal brush is simply too large to fit between tightly spaced teeth, between teeth and the orthodontic appliances or into the periodontal pockets. Utility of the interproximal brush is limited to spaces larger than the diameter of the twisted wire spines.

U.S. Pat. No. 5,,123,841 teaches a motorized version of the conical shaped interproximal brush, wherein the manual manipulation of the brush is augmented by a vibrating motion provided by the device. The advantage of the device over the manual interproximal brush is the increased number of strokes per unit of time resulting in improved cleaning efficiency. However, just like the manually operated interproximal brushes the device works only in large gaps and it fails to achieve the goal of plaque removal from tight spaces and from the periodontal pockets.

Periodontal pockets can be classified as normal when ranging from 1 to 2 mm deep, diseased but manageable when ranging from 3 to 5 mm deep, and seriously diseased requiring surgical intervention when deeper than 6 mm. The width of the diseased pockets, or the separation between the teeth 23 and the gums 25 as shown in FIG. 5 is typically less than 0.4 mm. U.S. Pat. No. 5,123,841 teaches that the ideal diameter of the twisted wire spine 40 of the conical interproximal brush shown in FIG. 7 is approximately 0.50 mm. It is easy to see that the spine of the interproximal brushes alone are so large that they can not enter the periodontal pockets typically less than 0.50 mm wide. As shown in FIG. 7, if cleaning of the pockets 32 is attempted from a radial direction of the interproximal brush 44, the penetration of any filament 42 is limited by the other filaments 42 contact with the gums 25 and the teeth 23.

The failures and disadvantages of the prior art are numerous and actually negating the advantages provided by the motorized vibratory motion. The radially extending bristles are supported by a twisted metal spine which enlarges the size of the brush and prevents it to enter into the smaller interproximal spaces between teeth, or between teeth and orthodontic appliances. The pointed end of the stiff metal spine enters into all interproximal areas first, and being mounted perpendicularly to the vibrating arm and vibrating in an axial direction like a spear, presents a real and substantial danger of unintentional cutting and piercing of the gums. It is easy to see that any attempt of cleaning the periodontal pockets of the gums would result in serious gum injury.

U.S. Pat. No. 5,123,841 teaches that the main object of his device is to vibrate the "feathers" or bristles in the cavity hundreds of times with tiny random movements and a burrowing action to flagellate the furcal areas with the ends of the bristles. This action is effective to remove plaque from the teeth enamel. However, since the axial vibration of the brush causes splaying of the bristles into the subgingival area, this axially burrowing and flagellating action of the sharp ends of the bristles can be dangerous and detrimental to soft and inflamed gingival tissues.

What has occurred to date is that not-withstanding the teachings of the prior art, the ability to completely and safely remove plaque from the interproximal areas in general and from the periodontal pockets in particular, remained unsolved.

OBJECTS AND ADVANTAGES OF THE INVENTION

Responding to the above described unresolved needs, the object of this invention is to provide a method and apparatus to safely remove plaque from the tightest interproximal spaces and from the deepest periodontal pockets.

An other object of the invention is to provide a plaque removal device which comprises of a single tuft of toothbrush filaments without a spine, vibrating in a orbital or reciprocal manner to ease the entrance of the filaments into smallest of interproximal spaces and into the periodontal pockets.

A further object of the invention is to assure that the orbital or reciprocal vibration of the bristles have no mechanized motion vector in the axial direction of the bristles to prevent the damaging of the gums by the ends of the filaments.

Yet another object of the invention is the generation of sonic or ultrasonic waves within the liquids filling the periodontal pockets to enhance the removal of plaque. Further objects and advantages will be apparent from the examination of the drawings and the claims.

BRIEF DESCRIPTION OF THE DRAWINGS

In the accompanying drawings, in which certain modes of carrying out the present invention are shown for illustrative purposes:

FIG. 4A, 4B, 4C, and 4D illustrates the step by step method of arranging the bristle tuft into a single line of filaments and positioning the filaments into the periodontal pockets.

FIG. 8 is a diagrammatic view illustrating the internal components and the orbital vibration pattern of the invention enhanced with an ultrasonic generator and transducer.

DESCRIPTION OF THE PREFERRED METHODS AND EMBODIMENTS

Figure 1:
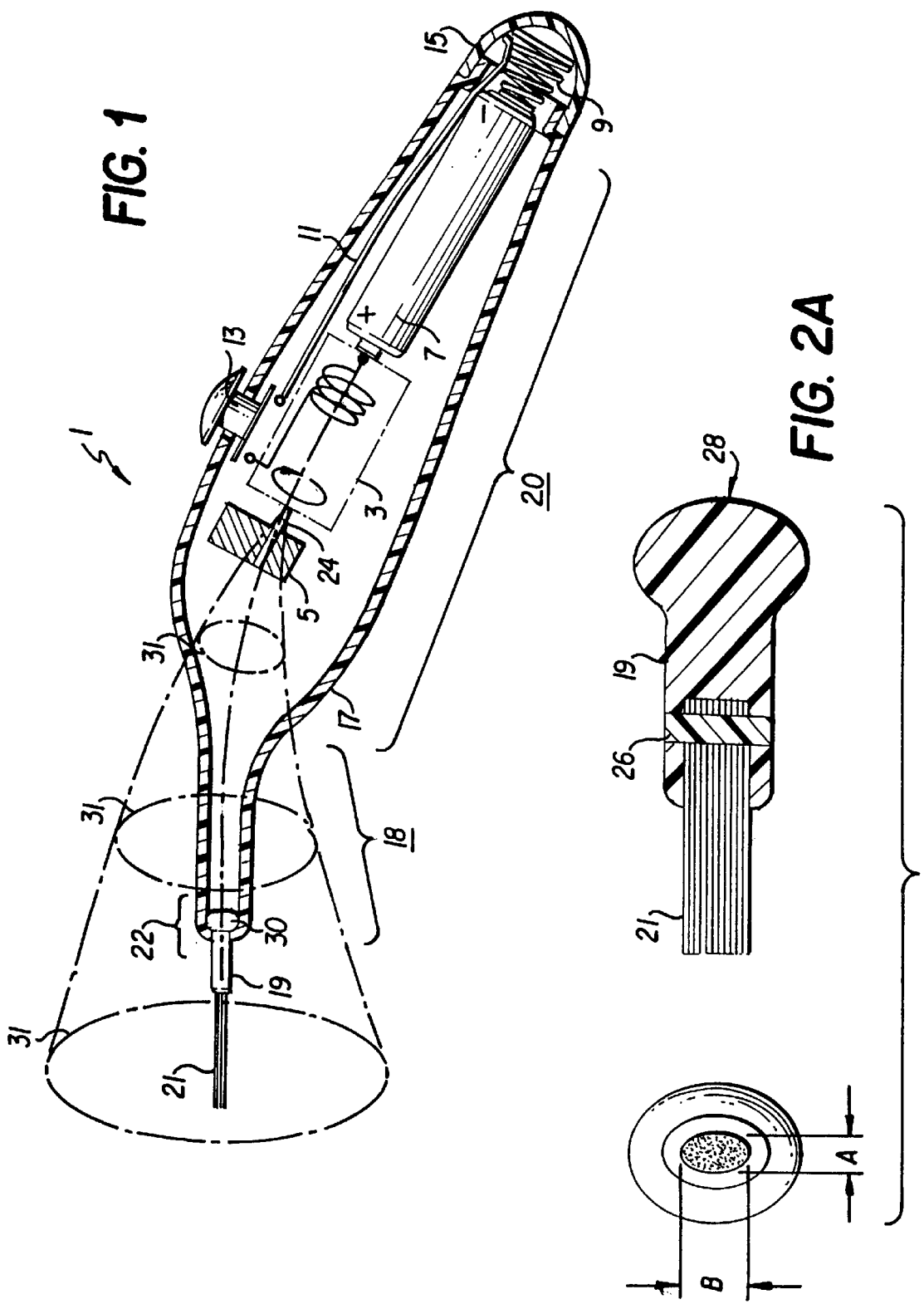
FIG. 1 is a diagrammatic view illustrating the internal components and the orbital vibration pattern of the invention.

Referring in detail to the drawings, the reference numerals herein refer to the like numbered parts in the drawings.

FIG. 1 shows a diagrammatic view of the preferred embodiment of the interproximal plaque removal device 1 having an elongated hollow handle 17 made of rigid plastic material which houses the electrical motor 3 driven by a replaceable battery 7. The motor 3 is secured firmly in the handle 17 by either a press fit or bit way of a strong adhesive. The positive electrode of the battery is held firmly against one of the electrical connections of motor 3 by a conical spring 9 enclosed in a removable cap 15 of the handle. In addition of holding the battery 7 against the motor 3 the conical spring 9 also functions as an electrical conductor to connect the negative electrode of the battery 7 to one of the terminals of switch 13 via an electrical conductor 11. The other terminal of switch 13 is connected to the second electrical connection of motor 3. Cap 15 is typically secured on the handle by threads or a bayonet locking system similar to the ones commonly found lens attachments to camera bodies. The main portion 20 of the handle 17 should be as small as possible to facilitate easy and comfortable handling of the device by children but large enough to provide space for the motor 3 and the battery 7. The front end portion 18 of the handle 17 should be tapered down to approximately one quarter of an inch in diameter to facilitate easy access to the oral cavity. The tip 22 portion of the handle contains a spherical recess 30 to removably secure a bristle holder 19 which carries a single tuft of nylon toothbrush filaments 21.

An eccentrically mounted weight 5 is firmly attached to the rotatable shaft 24 of the electric motor 3 by either a press fit or an adhesive. When switch 13 is closed by the user, it conducts electricity from the negative electrode of the battery 7 via the spring 9 and the conductor 11 to the motor, completing the electrical circuit, and motor 3 will rotate the eccentrically mounted weight 5. The eccentrically mounted rotating weight 5 will vibrate the entire device 1 in an orbital mode as shown by circles 31. The amplitude of the orbital vibration is smaller at the center of the handle where it is held by the user, and becomes larger and larger toward the unrestricted end 22 of the handle. The bristle filament tuft 21 will have the largest vibratory amplitude because it is the furthest away from the center of handle 17 and being constructed of highly flexible nylon filaments.

Figure 2:
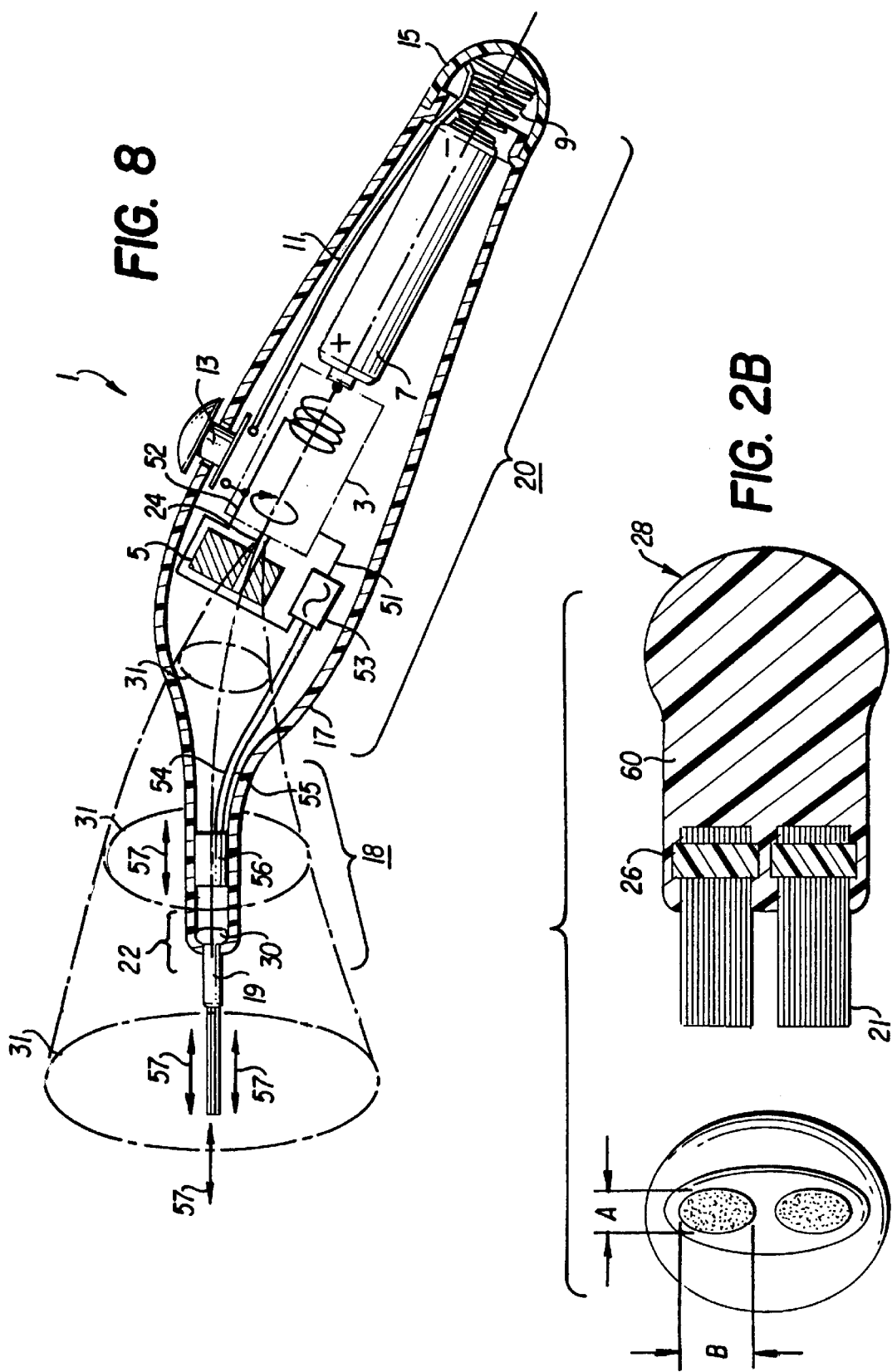
FIG. 2A shows a cross sectional view and an end view of the replaceable bristle head of the device containing a single tuft of bristles.
FIG. 2B shows a cross sectional view and an end view of the replaceable bristle head of the device containing two tufts of bristles.

FIG. 2A shows the construction of the removable bristle holder 19 containing a single tuft 21 of nylon toothbrush bristles secured in the holder 19 by a staple 26. The cavity of the holder 19 which receives the bristle tuft 21 is elliptically shaped, having a short axis A and a long axis B. The end portion 28 of the bristle holder 19 opposite to the bristle tuft 21 is spherically shaped and enlarged to facilitate the retention of the bristle holder 19 in the spherically recessed 30 end portion 22 of the handle 17.

FIG. 2B shows the construction of the removable bristle holder 19 containing two tufts 21 of nylon toothbrush bristles secured in the holder 19 by staples 26. The cavity of the holder 19 which receives the bristle tufts 21 is elliptically shaped, having a short axis A and a long axis B. The end portion 28 of the bristle holder 60 opposite to the bristle filament tufts 21 is spherically shaped and enlarged to facilitate the retention of the bristle holder 19 in the spherically recessed 30 end portion 22 of the handle 17.

Figure 3:
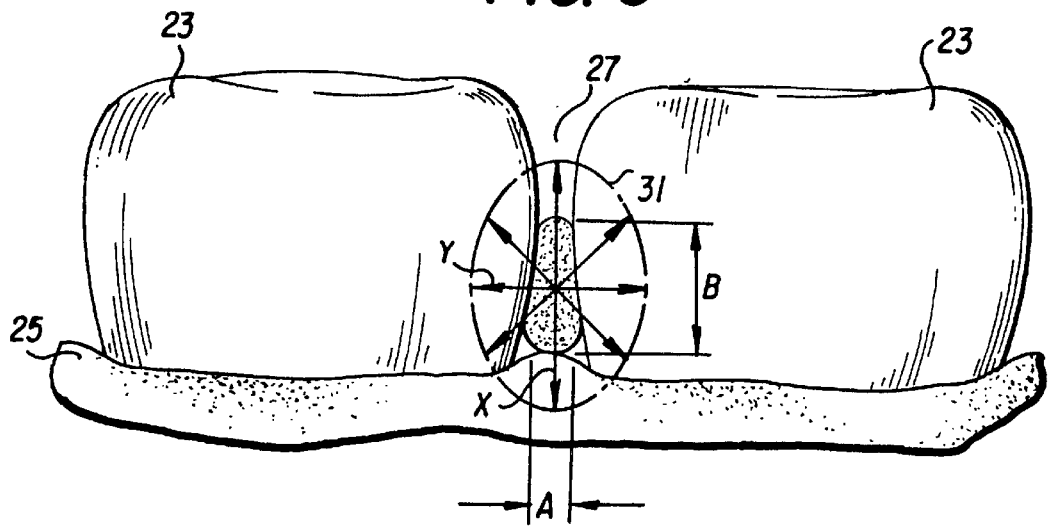
FIG. 3 shows the bristle tuft in operating position within the interproximal space between teeth and the gums.

FIG. 3 explains the reason for the elliptical cross sectional shape of the nylon bristle tuft 21. As shown in FIG. 3, the typical interproximal gap 27 formed between teeth 23 is long and narrow. Pre shaping the bristle tuft 21 in a similar shape facilitates the easy entrance of the nylon bristle tuft 21 into the interproximal gap 27. The orbital vibrating pattern 31 of the nylon bristle tuft 21 can be broken down to motion vectors in a full 360 degree circle. Particularly important vectors are X and Y.

Working on the plaque loaded surfaces of the teeth, vector Y pushes the bristle tuft 21 alternatively against the first and second teeth 23. Vector X provides a scrubbing motion of the surfaces forming the interproximal gap 27. Vector X pushes the bristle tuft 21 against the gum 25 in a pulsating motion while vector Y scrubs the surface of gum 25.

Figure 6:
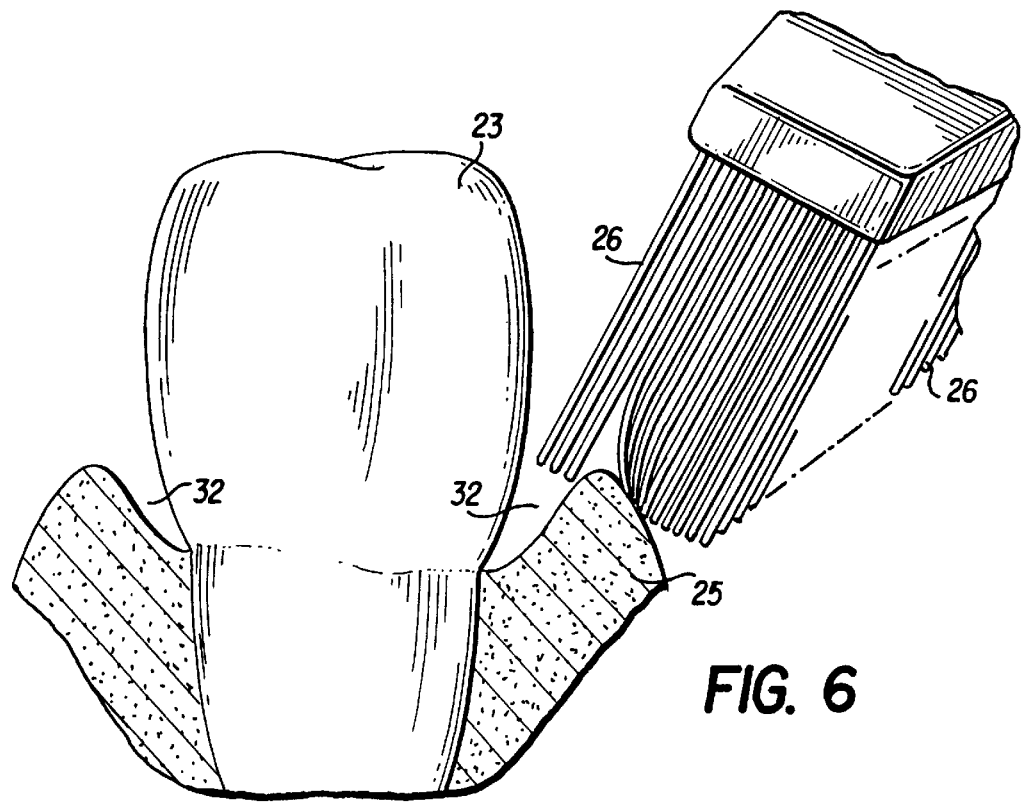
FIG. 6 illustrates the disadvantage of prior art, why the standard multitufted toothbrush can not penetrate the periodontal pockets.
Figure 7:
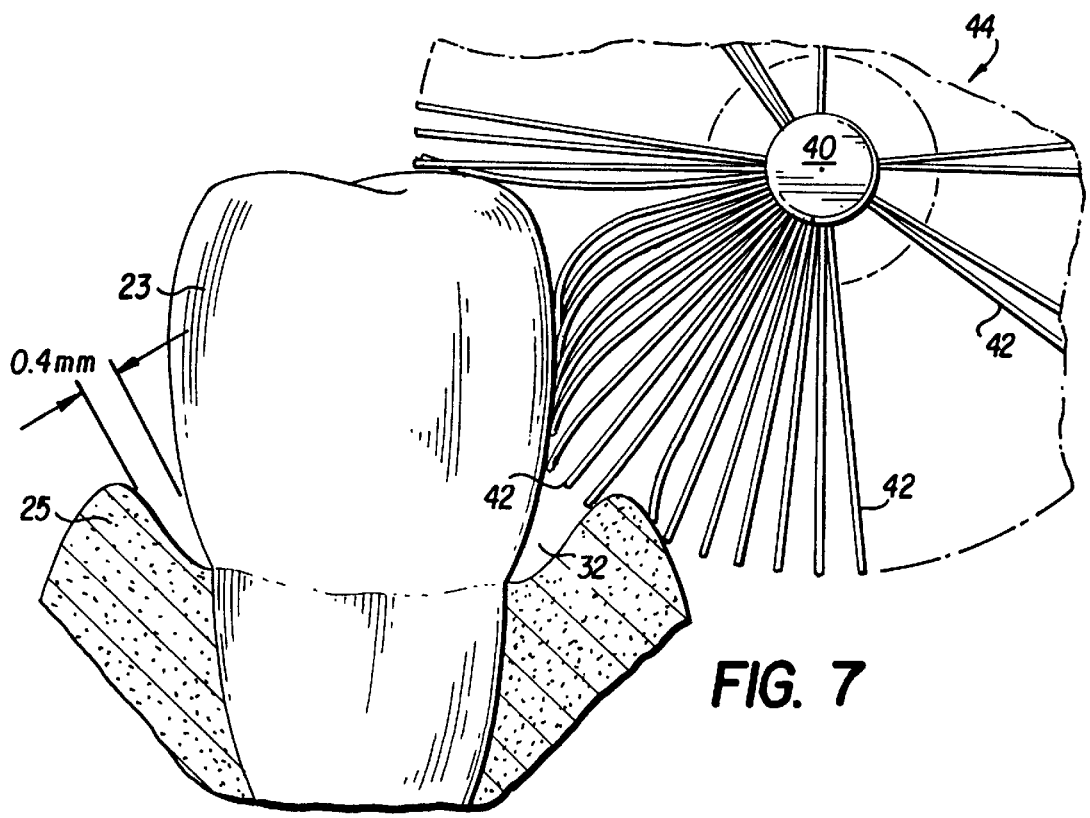
FIG. 7 illustrates the disadvantage of prior art, why the circular interdental toothbrush with twisted wire spine can not penetrate the periodontal pockets.

To maintain good dental hygiene, it is extremely important to remove the accumulation of plaque bacteria from the periodontal pockets on daily basis. Dental floss can clean between the teeth, but can not be maneuvered into the facial and lingual parts of the periodontal pockets. The best currently available device and process to clean the facial and lingual areas of the pockets is the common toothbrush. However, as demonstrated in FIG. 6, the common toothbrush can not penetrate deeper than perhaps 1 mm into the periodontal pockets, therefore it can not clean the pockets completely.

Figure 5:
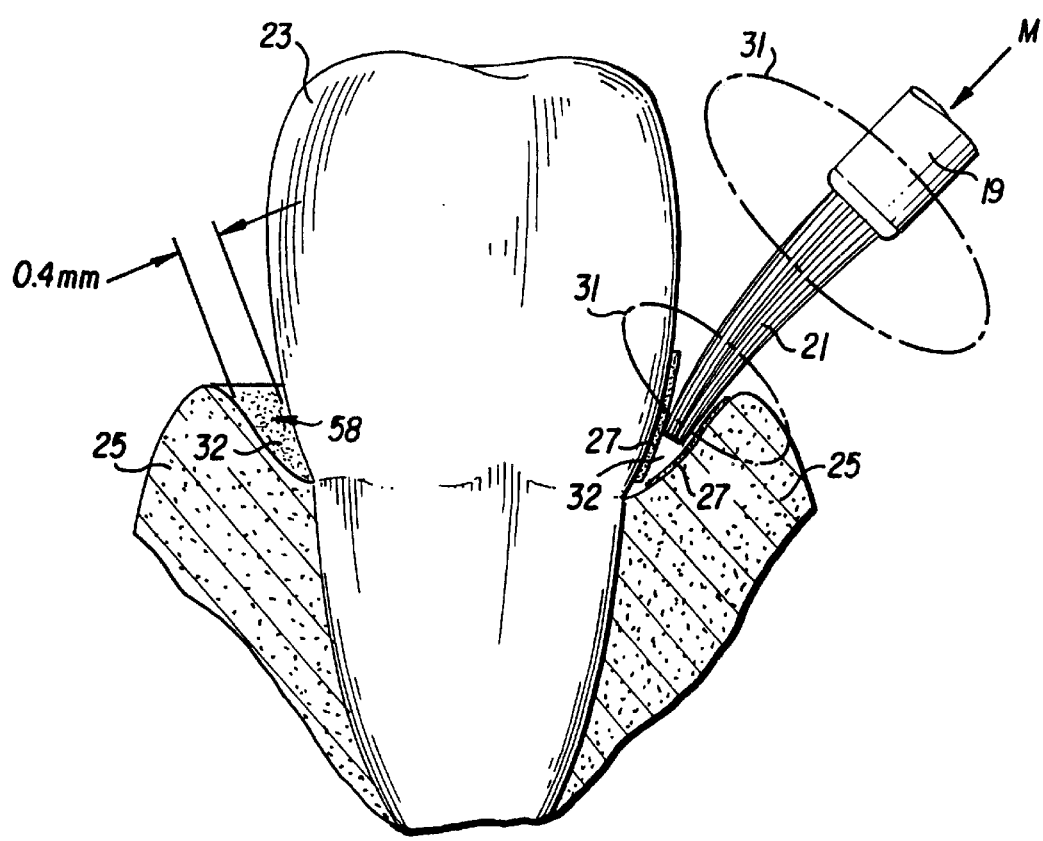
FIG. 5 illustrates the method of penetrating the periodontal pockets with the bristles of the invention and removing plaque from the periodontal pockets by the orbitally vibrating bristles.

The most significant and unique advantage of the interproximal plaque removal device 1 is described by FIG. 4A, 4B, 4C, 4D, and FIG. 5. As shown in FIG. 2A, the single bristle tuft 21 of the invention is elliptically shaped, ideally having a small axis A of approximately 1 mm and a large axis B of approximately 1.5 mm. Ideally the tuft is constructed of 0.1 mm diameter nylon bristles, just slightly smaller than the 0.2 to 0.4 mm width of the diseased periodontal pockets. As shown in FIG. 4A and 4B, the user positions bristle tuft 21 of the invention along the lingual or facial surface of the teeth 23 above the periodontal pocket 32 and activates the device. The tuft of bristles 21 began to vibrate orbitally along the circle 31. Next, as shown in FIG. 4C and 4D, the user presses the bristle tuft 21 against the surface of the tooth 23 in the direction of the arrow Z. The orbital vibratory motion 31 helps the tuft to spread into a single layer of bristles in the direction of the large axis B and to reduce the dimension of the elliptical configuration of the bristle tuft 21 in the direction of the small axis A into line of one or two bristles, or 0.1 to 0.2 mm. Since the typical periodontal pockets are 0.2 to 0.4 mm wide, the user can proceed to comfortably and safely advance the now linearly shaped bristle tuft 21 into the periodontal pocket in the direction of arrow M as shown in FIG. 5. Slightly relaxing his fingers, the user allow the orbital vibration 31 of the bristle tuft 21 to alternately scrub and remove plaque 27 from the surfaces of the tooth 23 and the gum 25 to the full depth of the periodontal pocket 32. Since the scrubbing of the surfaces of the tooth 23 and the gum 25 is done by the orbitally vibrating smooth cylindrical surfaces of the bristles, and there is no mechanized motion vector in the axial direction which would drive the points of the bristles into the gums, ultimate safety is assured. In addition to the mechanical scrubbing, the bristles set up standing sonic pressure waves within the gingival fluids in the periodontal pockets. These standing sonic pressure waves augment the scrubbing forces of the bristles and also aid in the breaking loose and removal of plaque bacteria from the minute cracks and crevices on the surfaces of the teeth and gums not reachable physically by the bristles.

To enhance removal of tartar from the teeth, dentists are using commercially available ultrasonic scalers. Periodontists often utilize the same scalers for below the gumline debridement, or removal of calcified and semi calcified plaque from the root of the teeth. These ultrasonic scalers vibrate a solid metal tip which contacts the surface of tooth but should not come in contact with the soft tissue of the gums. If the ultrasonically vibrating metal tip contacts the tissue, it will either burn or cut the tissue causing significant damage. The ultrasonically vibrating metal tip set up a pattern of ultrasonic pressure waves within the gingival fluid in the pockets which helps the removal of tartar both from the areas touched by the metal tip and beyond. While the ultrasonic scaler is an excellent tool in the hands of a trained medical professional, they present unacceptable dangers in the hands of a layman. These devices can not be used safely by a person at home.

An enhanced embodiment of the invention is illustrated in FIG. 8 by adding an ultrasonic generator 53 connected to the battery power by conductors 51 and 52, producing ultrasonic frequency electrical pulses in the range of 10 kHz and 20 MHz which are transmitted from the generator 53 to an ultrasonic transducer 56 located within the tip 18 portion of the interproximal plaque removal device 1 via conductors 54 and 55. The transducer 56 is secured within the handle 17 by press fit or by epoxy adhesive. The ultrasonic vibrations 57 generated by the transducer are coupled by the bristle holder 19 to the bristle tuft 21. The ultrasonically enhanced bristle tuft 21 transmits the ultrasonic vibrations 57 into the gingival fluids in the periodontal pockets, producing standing ultrasonic waves within the gingival fluids 58 which augments and enhances the plaque removal capability of the nylon bristle tufts 21. Contrary to the metal tipped professional ultrasonic scalers to remove hard tartar, the ultrasonically enhanced bristles are made of soft nylon therefore are completely safe in the hands of a laymen to be used routinely at home for the daily removal of soft plaque before it has a chance to calcify into tartar.

Figure 9:
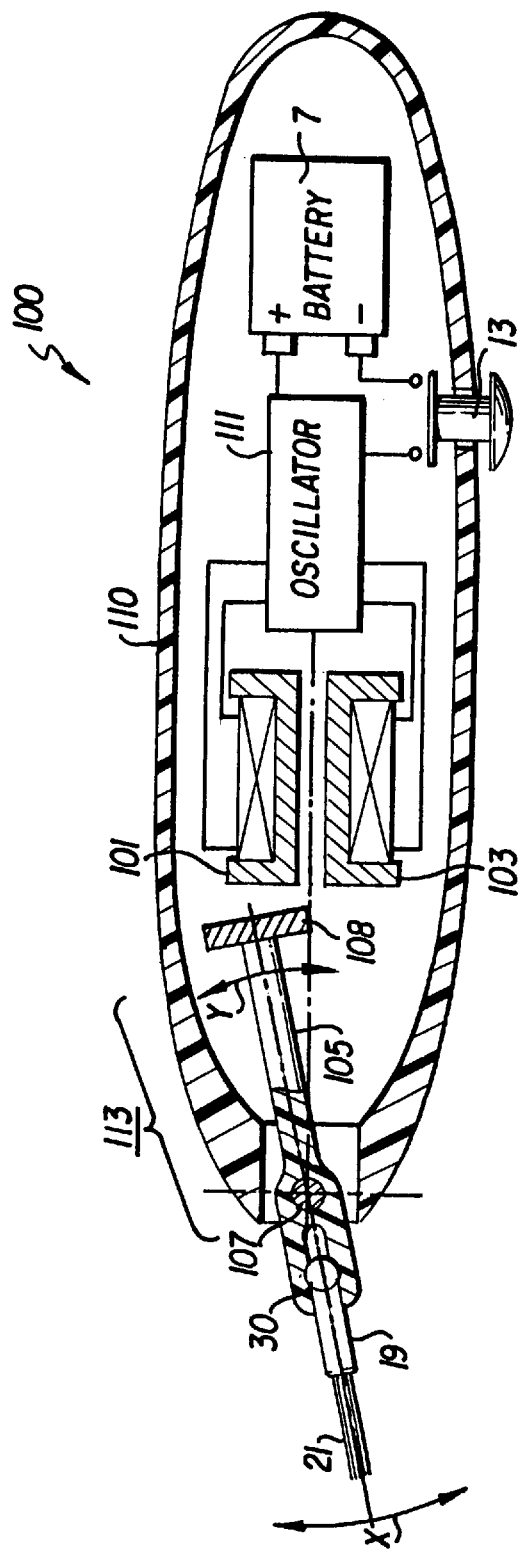
FIG. 9 is a diagrammatic view illustrating an other embodiment of the internal components and the reciprocal vibration pattern of the invention.

FIG. 9 shows a diagrammatic view of an embodiment of the interproximal plaque removal device 100 having an elongated hollow handle 110 made of rigid plastic material which houses two electro magnets 101 and 103 alternatively energized by an electronic oscillator 111 powered by a battery 7. The electro magnets 101 and 103 are secured firmly in the handle 110 by either a press fit or by way of a strong adhesive. The positive terminal of the battery 7 is connected directly to the oscillator 111 while the negative terminal of battery 7 is connected to the oscillator 111 through switch 13. The tip 113 portion of the handle 110 contains a pivot pin 107 securing the reciprocally vibrating arm 105 to the handle 110. One end of arm 105 contains a spherical recess 30 to removably secure a bristle holder 19 which carries a single tuft of nylon toothbrush filaments 21. The other end of arm 105 carries a permanent magnet 108.

As switch 13 is closed by the user, it conducts electricity from the negative electrode of the battery 7 to the oscillator 111. The oscillator 111 will alternatively energize the electro magnets 101 and 103, which in turn pull the permanent magnet alternatively toward magnets 101 and 103 imparting a reciprocally vibrating motion to the magnet 108. As the magnet 108 oscillates between the electro magnets 101 and 103 the arm 105 pivots around pin 107, imparting a side to side reciprocating vibratory motion to the other end of the arm 105 carrying the bristle holder 19 and the toothbrush filaments 21. The construction of the bristle holder 19 and the single tuft of filaments 21 have been described in the earlier embodiments, and can be substituted by multiple tuft design as shown in FIG. 2A and 2B.

A further enhancement of the performance of the reciprocally vibrating bristles described in this embodiment can be achieved by the addition of an ultrasonic frequency generator in the handle 110 and the placement of an ultrasonic transducer in the arm 105 to ultrasonically charge the bristles. The ultrasonic frequency generator and the ultrasonic transducer were described earlier in reference to the orbitally vibrating bristles in FIG. 8 as items 53 and item 56 respectively.

While the preceding description contain many specificities, these should not be construed as limitations on the scope of the invention, but rather as exemplification of a preferred and additional embodiments thereof. Many other variations are possible. Skilled artisans will readily be able to change dimensions, shapes and construction materials of the various components described in the embodiments. Accordingly, the scope of the invention should be determined not by the embodiments illustrated, but by the appended claims and their legal equivalents.

What is claimed:

1. The method of facilitating the removal of plaque from the periodontal pockets of the dental anatomy defined by the external surfaces of the necks and roots of teeth and the internal surfaces of the gum separated from said necks and said roots of teeth comprising, inserting at least one bristle tuft into said periodontal pocket, inducing reciprocal vibration of said bristle tuft about the longitudinal axis of said bristle tuft of sufficiently high intensity to cause removal of said plaque from the said neck and root surfaces of teeth and said internal surfaces of gum by the friction generated between the cylindrical surfaces of said bristles and said plaque covering said neck and said root surfaces of teeth and said internal surface of gum by said reciprocal vibration of said bristle tufts.

2. The method as defined in claim 1 wherein the step of inducing said reciprocal vibrations of said tuft of bristles preceding the step of inserting said tuft of bristles into said periodontal pocket.

3. The method as defined in claim 2 wherein said tuft of bristles are also imparting ultrasonic wave vibrations to the gingival fluids between said neck and said root surfaces of teeth and said internal surface of gum.

* * * * *